United States Patent
Lee et al.

(10) Patent No.: US 8,569,491 B2
(45) Date of Patent: *Oct. 29, 2013

(54) METHOD FOR PREPARING ENTECAVIR AND INTERMEDIATE USED THEREIN

(75) Inventors: Jae Heon Lee, Yongin-si (KR); Gha Seung Park, Yongin-si (KR); Jin Hee Kim, Hwaseong-si (KR); Tae Jin Choi, Seongnam-si (KR); Ji Eun Lee, Seoul (KR); Jung Hee Han, Daejeon (KR); Hyo Jeong Bang, Yongin-si (KR); Sun Young Jung, Daejeon (KR); Young Kil Chang, Seoul (KR); Gwan Sun Lee, Seoul (KR); Maeng Sup Kim, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/501,414

(22) PCT Filed: Sep. 15, 2010

(86) PCT No.: PCT/KR2010/006306
§ 371 (c)(1),
(2), (4) Date: Apr. 11, 2012

(87) PCT Pub. No.: WO2011/046303
PCT Pub. Date: Apr. 21, 2011

(65) Prior Publication Data
US 2012/0202998 A1      Aug. 9, 2012

(30) Foreign Application Priority Data

Oct. 12, 2009 (KR) .................. 10-2009-0096875
Mar. 5, 2010 (KR) .................. 10-2010-0020106

(51) Int. Cl.
*C07D 473/00* (2006.01)

(52) U.S. Cl.
USPC ...................................... 544/276

(58) Field of Classification Search
USPC .......................................... 544/276
See application file for complete search history.

(56) References Cited

U.S. PATENT DOCUMENTS

| 5,206,244 A | 4/1993 | Zahler et al. |
| 7,381,746 B2 * | 6/2008 | Yasuhara et al. ............. 514/561 |
| 2005/0272932 A1 | 12/2005 | Zhou et al. |

FOREIGN PATENT DOCUMENTS

| CN | 100379736 C | 4/2008 |
| KR | 10-2009-0084979 A | 8/2009 |
| WO | 98/09964 A1 | 3/1998 |
| WO | 2004/052310 A2 | 6/2004 |
| WO | WO 2010/074534 A2 * | 7/2010 |

OTHER PUBLICATIONS

Greene, Theodora W., and Peter G. M. Wuts. Protective Groups in Organic Synthesis. n.p.: Wiley, 1999. eBook Collection (EBSCOhost).*
Wermuth, Camille G., The Practice of Medicinal Chemistry. Academic Press Limited, 1996.*
International Search Report of PCT/KR2010/006306 dated Jun. 23, 2011.
Kramer et al., "Divergent Synthesis and Biological Evaluation of Carbocyclic *alpa*-, *iso*- and 3'-*epi*-Nucleosides and their Lipophilic Nucleotide Products," Synthesis, 2006, No. 8, pp. 1313-1324.
Ziegler et al., "Radical Cyclization Studies Directed Toward the Synthesis of BMS-200475 'entecavir': the Carbocyclic Core," Tetrahedron, 2003, vol. 59, pp. 9013-9018.
Taiwanese Patent Office, Taiwanese Office Action issued in corresponding TW Application No. 099134574, dated Sep. 17, 2012.
European Patent Office, European Search Report issued in corresponding EP Application No. 10823545.8, dated May 2, 2013.

* cited by examiner

*Primary Examiner* — Noble Jarrell
*Assistant Examiner* — Laura Daniel
(74) *Attorney, Agent, or Firm* — Sughrue Mion, PLLC

(57) ABSTRACT

Disclosed are a novel, high-yield method for preparing entecavir and intermediates used therein.

24 Claims, 1 Drawing Sheet

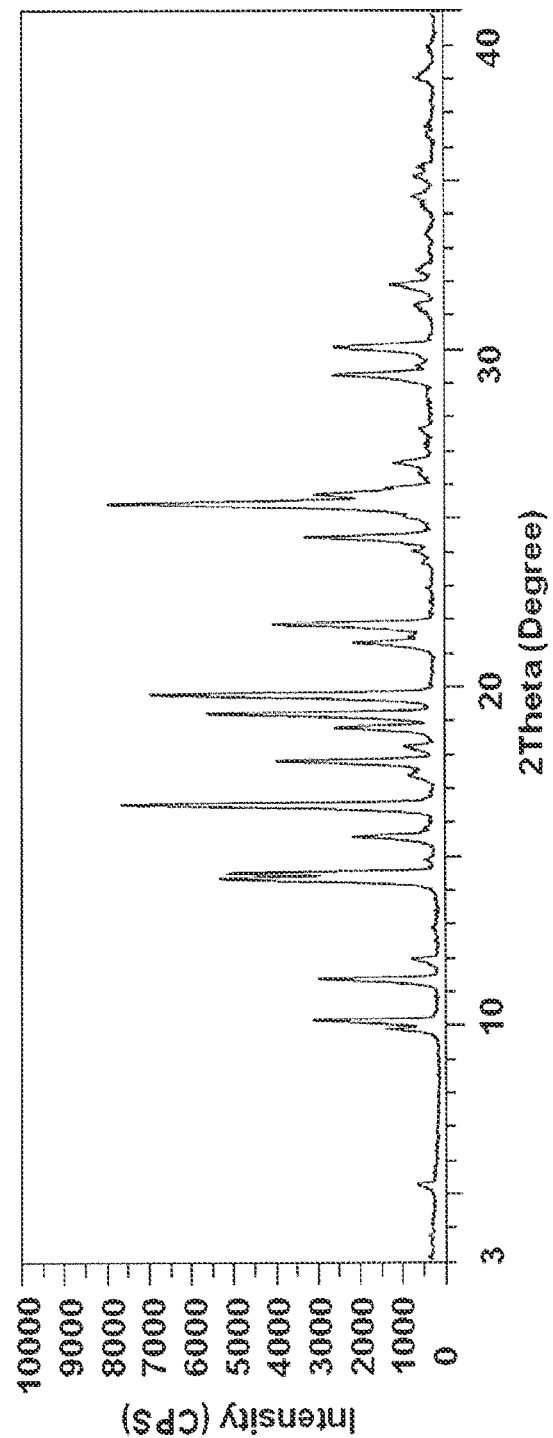

METHOD FOR PREPARING ENTECAVIR AND INTERMEDIATE USED THEREIN

CROSS REFERENCE TO RELATED APPLICATIONS

This application is a National Stage of International Application No. PCT/KR2010/006306 filed Sep. 15, 2010, claiming priority based on Korean Patent Application Nos. 10-2009-0096875 filed Oct. 12, 2009 and 10-2010-0020106 filed Mar. 5, 2010, the contents of all of which are incorporated herein by reference in their entirety.

FIELD OF THE INVENTION

The present invention relates to a novel method for preparing entecavir and intermediates used therein.

BACKGROUND OF THE INVENTION

Entecavir, [1-S-(1α,3α,4β)]-2-amino-1,9-dihydro-9-[4-hydroxy-3-(hydroxymethyl)-2-methylenecyclopentyl]-6H-purin-6-one, is currently used for treating hepatitis B virus infection, whose structure is composed of a cyclopentane ring having purine, exomethylene, hydroxymethyl, and hydroxy substituents at the 1S-, 2-, 3R-, and 4S-positions, respectively.

There have been conducted a number of studies to develop methods for preparing entecavir. For example, U.S. Pat. No. 5,206,244 and WO 98/09964 disclose a method for preparing entecavir as shown in Reaction Scheme 1:

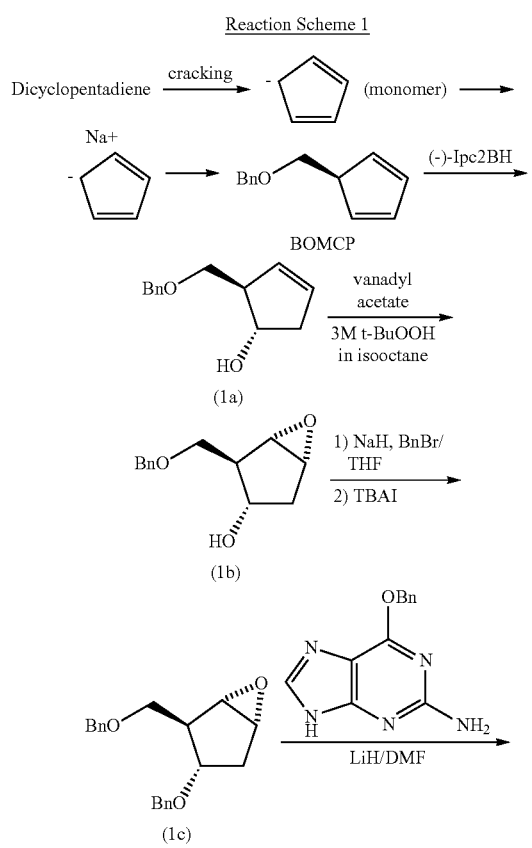

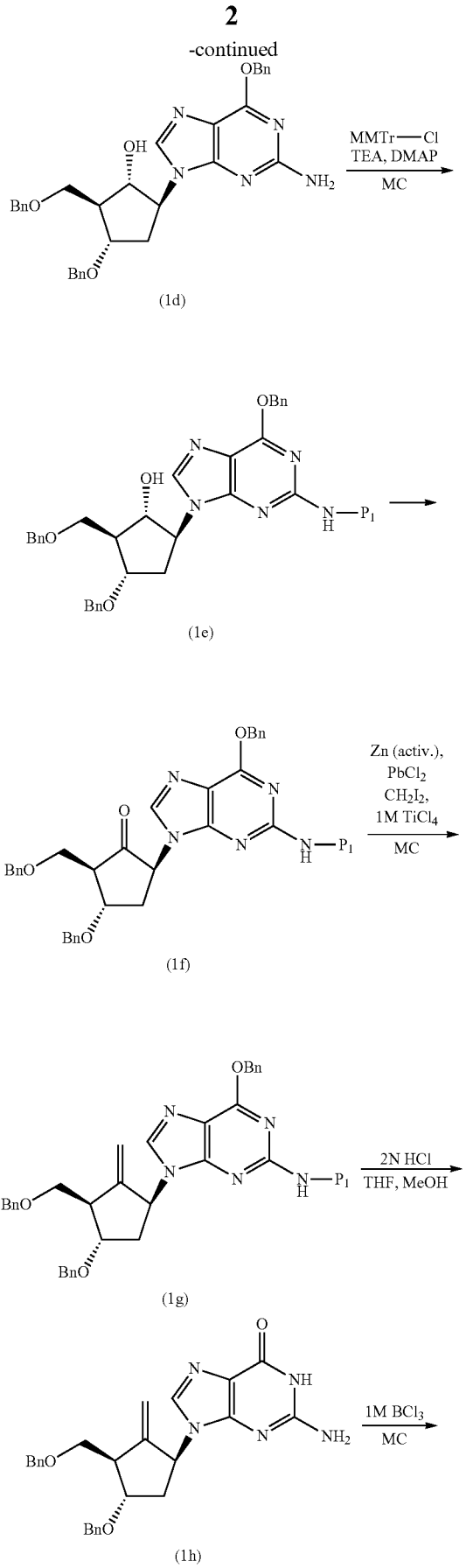

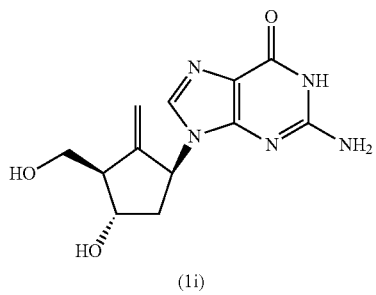

(1i)

wherein P₁ is trityl or substituted trityl, Bn is benzyl, BOMCP is benzyloxymethylcyclopentadiene, IpcBH is diisopinocampheylborane, DMAP is N,N-dimethyl-4-aminopyridine, DMF is dimethylformamide, MC is methylene chloride, MMTr-Cl is 4-monomethoxytrityl chloride, TBAI is tetrabutylammonium iodide, TEA is triethylamine, and THF is tetrahydrofurane.

The above method, however, has difficulties in that: i) the cyclopentadiene monomer must be maintained at a temperature lower than −30° C. in order to prevent its conversion to dicyclopentadiene; ii) residual sodium after the reaction as well as the sensitivity of the reaction toward moisture cause problems; iii) the process to obtain the intermediate of formula (1a) must be carried out at an extremely low temperature of below −70° C. in order to prevent the generation of isomers; iv) a decantation method is required when (−)-Ipc₂BH (diisopinocampheylborane) is used for hydroboration; v) the process for preparing the intermediate of formula (1e) does not proceed smoothly; and, vi) separation by column chromatography using MCI GEL™ CHP-20P resin (Sigma-Aldrich) is required to purify entecavir.

WO 2004/52310 and U.S. Pat. Publication No. 2005/0272932 disclose a method for preparing entecavir using the intermediate of formula (2f) which is prepared as shown in Reaction Scheme 2:

Reaction Scheme 2

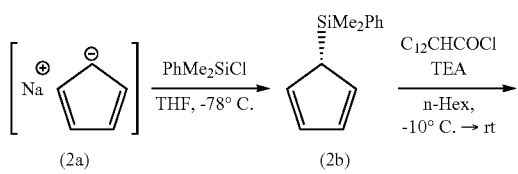

(2a)     (2b)

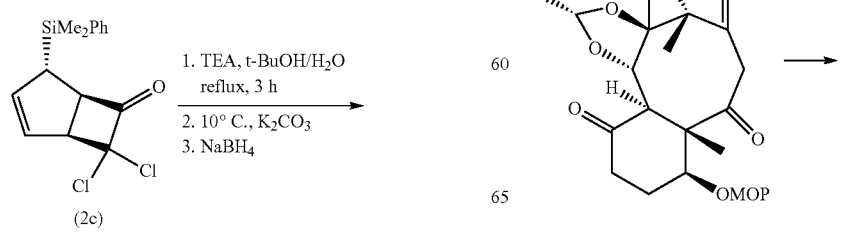

(2c)

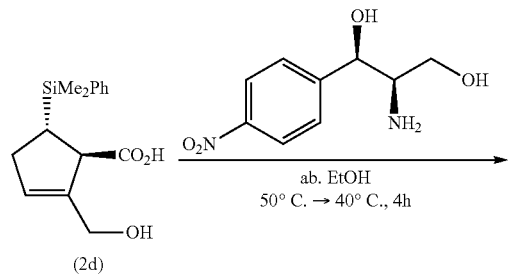

(2d)

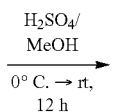

(2e)

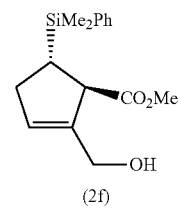

(2f)

wherein, Me is methyl, t-Bu is t-butyl, Et is ethyl, n-Hex is n-hexane and Ph is phenyl.

The above method for preparing the intermediate of formula (2b) must be carried out at an extremely low temperature of −70° C. or less, and the yield of the desired product (2f) in the optical resolution step is less than 50%.

Various methods for preparing triflic enolate have been developed. For example, the document ["Preparation of allylsilane 12", *J. Am. Chem. Soc.*, 1998, 120, 12980-12981] has disclosed a method for preparing triflic enolate comprising the step of conducting regioselective reaction of potassium hexamethyl disilazane (KHMDS) with N-phenyl triflimide (PhNTf₂) as described in reaction scheme 3. U.S. Pat. No. 7,381,746 B2 has disclosed a method for preparing triflic enolate as described in reaction scheme 4. The document [*J. Chem. Soc.*, Perkis Trans. 1, 2000, 345-351] has also disclosed a method for preparing triflic enolate.

Reaction Scheme 3

-continued

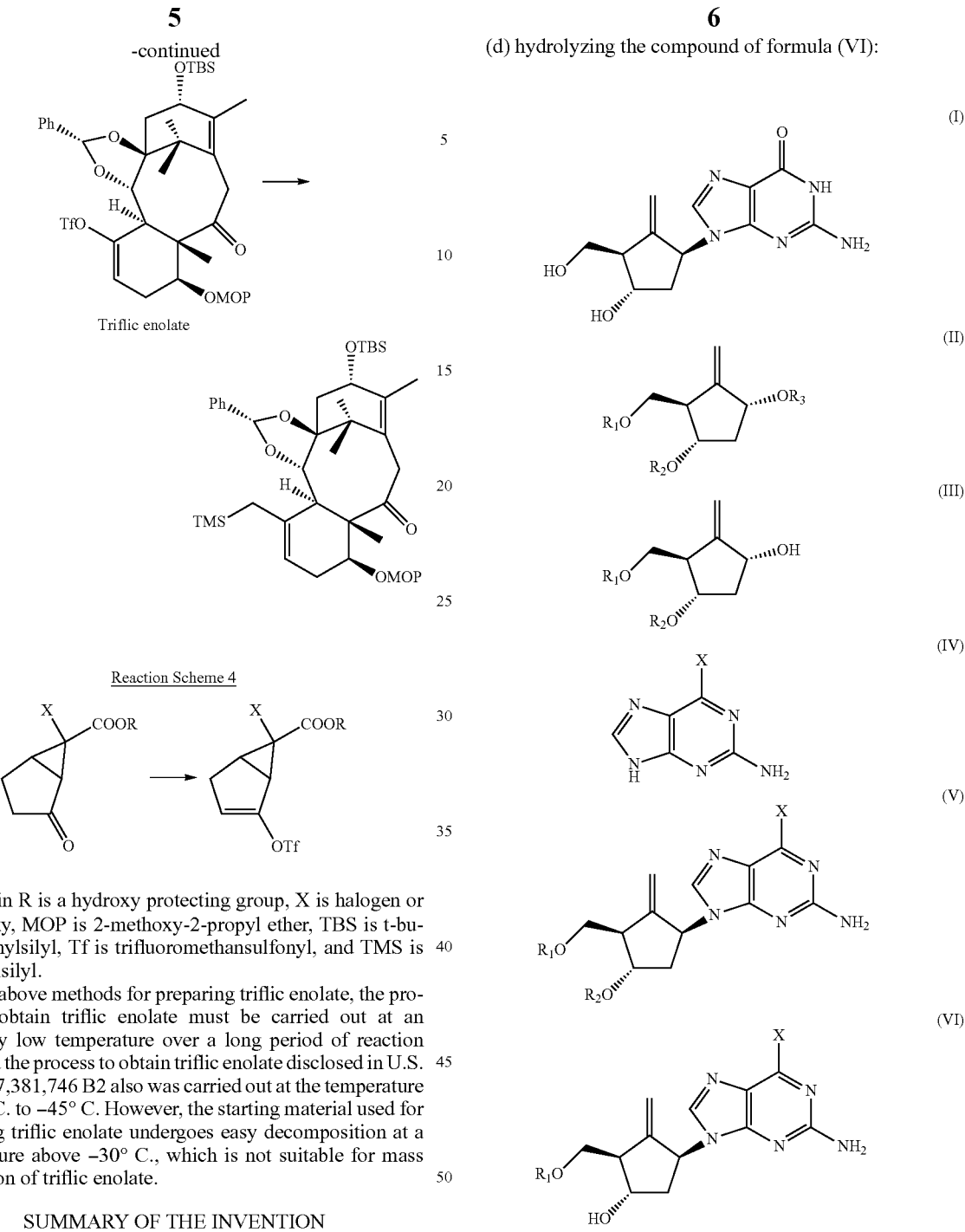

wherein R is a hydroxy protecting group, X is halogen or benzyloxy, MOP is 2-methoxy-2-propyl ether, TBS is t-butyldimethylsilyl, Tf is trifluoromethansulfonyl, and TMS is trimethylsilyl.

In the above methods for preparing triflic enolate, the process to obtain triflic enolate must be carried out at an extremely low temperature over a long period of reaction time, and the process to obtain triflic enolate disclosed in U.S. Pat. No. 7,381,746 B2 also was carried out at the temperature of −63° C. to −45° C. However, the starting material used for preparing triflic enolate undergoes easy decomposition at a temperature above −30° C., which is not suitable for mass production of triflic enolate.

SUMMARY OF THE INVENTION

Accordingly, it is an object of the present invention to provide a novel, high-yield method for preparing entecavir and novel intermediates used therein.

In accordance with an aspect of the present invention, there is provided a method for preparing entecavir of formula (I), comprising the steps of:

(a) hydrolyzing an a-exomethylene derivative of formula (II) to obtain a compound of formula (III);

(b) carrying out a Mitsunobu reaction of the compound of formula (III) with a purine derivative of formula (IV) to obtain a nucleoside compound of formula (V);

(c) subjecting the nucleoside compound of formula (V) to a reaction with tetrabutyl ammonium fluoride to obtain a compound of formula (VI); and (d) hydrolyzing the compound of formula (VI):

wherein
$R_1$ and $R_2$ are each independently a hydroxy-protecting group, or $R_1$ and $R_2$ are fused together to form a cyclic hydroxy-protecting group;
$R_3$ is benzoyl or arylbenzoyl, preferably benzoyl or 4-phenylbenzoyl;
Tf is trifluoromethane sulfonyl; and
X is halogen or benzyloxy.

In accordance with another aspect of the present invention, there are provided the α-exomethylene derivative of formula (II), a β-exomethylene derivative of formula (VII), an epoxide derivative of formula (VIII), a compound of formula (IX), a triflic enolate derivative of formula (X), and a compound of formula (XIII), which are used in the preparation of entecavir of formula (I) or a solvate thereof, as an intermediate:

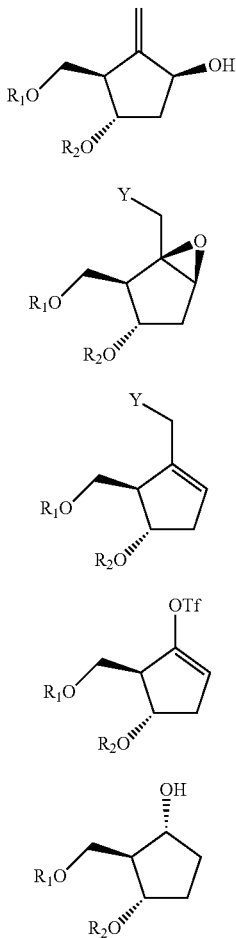

wherein,
R$_1$, R$_2$ and Tf are the same as defined above, and Y is alkylsilyl or arylsilyl.

In accordance with further aspect of the present invention, there are provided a solvate of crystalline entecavir dimethylformamide of formula (XIV) whose X-ray diffraction (hereinafter, referred to XRD) spectrum obtained using Cu-Kα radiation shows peaks having a peak intensity of 10% or more at diffraction angles (2θ±0.2) of 10.2, 14.4, 14.5, 16.6, 17.9, 18.8, 19.3, 19.8, 21.4, 21.9, 24.5, 25.5, 25.8, 26.7, 29.3, and 30.2; and a preparation method thereof:

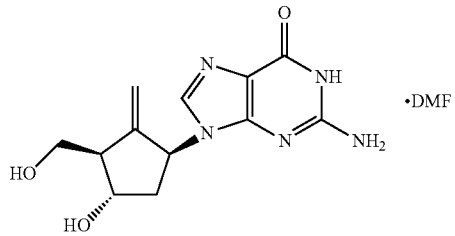

wherein, DMF is dimethylformamide.

BRIEF DESCRIPTION OF THE DRAWINGS

The above and other objects and features of the present invention will become apparent from the following description of the invention, when taken in conjunction with the accompanying drawings which respectively show:

FIG. 1: an XRD spectrum of the inventive compound of formula (XIV).

DETAILED DESCRIPTION OF THE INVENTION

As used herein, the term "alkyl" refers to a straight or branched chain saturated C$_1$ to C$_6$ hydrocarbon radical. Examples of "alkyl" as used herein include, but are not limited to, methyl, ethyl, n-propyl, isopropyl, n-butyl, isobutyl, t-butyl, n-pentyl, isopentyl, and hexyl.

As used herein, the term "alkoxy" refers to the group —OR$_a$, wherein R$_a$ is alkyl, as defined above. Examples of "alkoxy" as used herein include, but are not limited to, methoxy, ethoxy, n-propoxy, isopropoxy, n-butoxy, and t-butoxy.

As used herein, the term "aryl" refers to a C$_6$-C$_{18}$ aromatic hydrocarbon radical. The aromatic hydrocarbon radical comprises an optionally substituted mono- or bi-cyclic aromatic ring system (e.g., phenyl or substituted phenyl), and a fused ring system (e.g., naphthyl or phenatrenyl). Examples of "aryl" include, but are not limited to, phenyl, toluyl, xylyl, biphenyl, and naphthyl.

As used herein, the term "hydroxy-protecting group" refers to, for example, methyl having one, two, or three phenyl substituents (e.g., benzyl, trityl, or diphenylmethyl); benzyl substituted with alkoxy or nitro (e.g., methoxybenzyl or p-nitrobenzyl); benzoyl optionally substituted with alkoxy or nitro (e.g., benzoyl, methoxybenzoyl or p-nitrobenzoyl); silyl optionally substituted with at least one selected from the group consisting of alkyl and aryl (e.g., trimethylsilyl, triethylsilyl, isopropyldimethylsilyl, t-butyldimetylsilyl, t-butyldiphenylsilyl, or hexyldimethylsilyl); allyl; alkoxyalkyl (e.g., methoxymethyl or (2-methoxyethoxy)methyl); and tetrahydropyranyl; preferably trityl, benzoyl, and t-butyldiphenylsilyl; and most preferably trityl or t-butyldiphenylsilyl.

As used herein, the term "cyclic hydroxy-protecting group" refers to, for example, benzylidene, naphthylidene, 4-phenylbenzylidene, cyclic acetal, cyclic ketal, cyclic carbonate, cyclic orthoester, and cyclic 1,3-(1,1,3,3-tetraisopropyl)disiloxanediyl.

The method for preparing entecavir of formula (I) according to the present invention is shown in Reaction Scheme 5, but not limited thereto:

Reaction Scheme 5

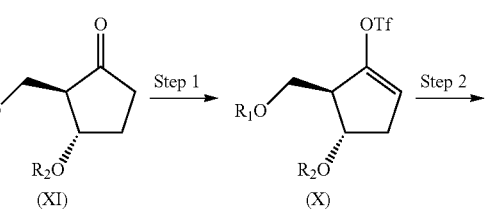

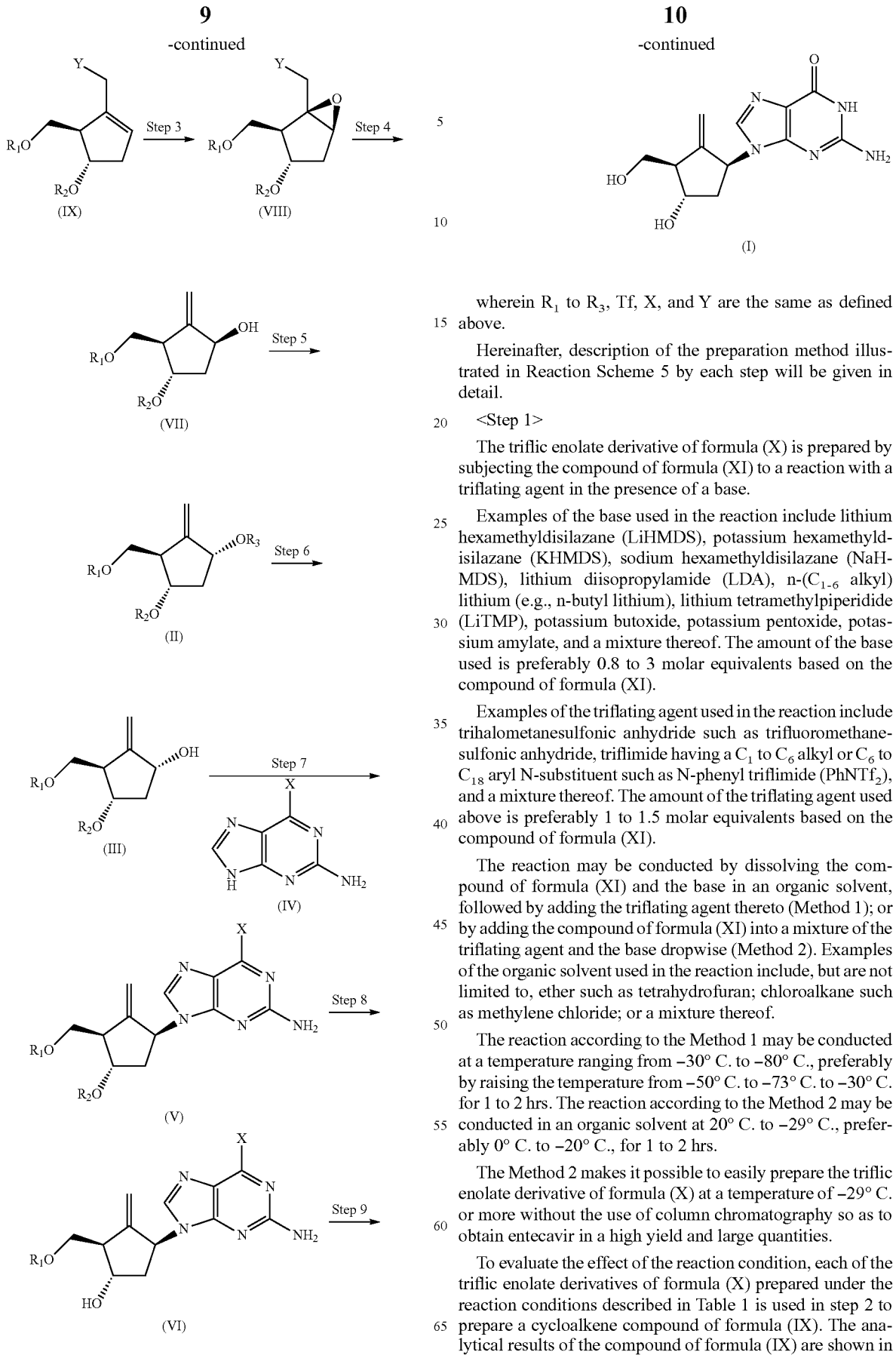

wherein $R_1$ to $R_3$, Tf, X, and Y are the same as defined above.

Hereinafter, description of the preparation method illustrated in Reaction Scheme 5 by each step will be given in detail.

<Step 1>

The triflic enolate derivative of formula (X) is prepared by subjecting the compound of formula (XI) to a reaction with a triflating agent in the presence of a base.

Examples of the base used in the reaction include lithium hexamethyldisilazane (LiHMDS), potassium hexamethyldisilazane (KHMDS), sodium hexamethyldisilazane (NaHMDS), lithium diisopropylamide (LDA), n-($C_{1-6}$ alkyl) lithium (e.g., n-butyl lithium), lithium tetramethylpiperidide (LiTMP), potassium butoxide, potassium pentoxide, potassium amylate, and a mixture thereof. The amount of the base used is preferably 0.8 to 3 molar equivalents based on the compound of formula (XI).

Examples of the triflating agent used in the reaction include trihalomethanesulfonic anhydride such as trifluoromethanesulfonic anhydride, triflimide having a $C_1$ to $C_6$ alkyl or $C_6$ to $C_{18}$ aryl N-substituent such as N-phenyl triflimide (PhNTf$_2$), and a mixture thereof. The amount of the triflating agent used above is preferably 1 to 1.5 molar equivalents based on the compound of formula (XI).

The reaction may be conducted by dissolving the compound of formula (XI) and the base in an organic solvent, followed by adding the triflating agent thereto (Method 1); or by adding the compound of formula (XI) into a mixture of the triflating agent and the base dropwise (Method 2). Examples of the organic solvent used in the reaction include, but are not limited to, ether such as tetrahydrofuran; chloroalkane such as methylene chloride; or a mixture thereof.

The reaction according to the Method 1 may be conducted at a temperature ranging from −30° C. to −80° C., preferably by raising the temperature from −50° C. to −73° C. to −30° C. for 1 to 2 hrs. The reaction according to the Method 2 may be conducted in an organic solvent at 20° C. to −29° C., preferably 0° C. to −20° C., for 1 to 2 hrs.

The Method 2 makes it possible to easily prepare the triflic enolate derivative of formula (X) at a temperature of −29° C. or more without the use of column chromatography so as to obtain entecavir in a high yield and large quantities.

To evaluate the effect of the reaction condition, each of the triflic enolate derivatives of formula (X) prepared under the reaction conditions described in Table 1 is used in step 2 to prepare a cycloalkene compound of formula (IX). The analytical results of the compound of formula (IX) are shown in Table 1.

TABLE 1

| | Compound of formula (XI) (g) | Triflic enolate derivative of formula (X) | | | | Yield of the cycloalkene compound of formula (IX) |
|---|---|---|---|---|---|---|
| | | LiHMDS (eq) | PhNTf$_2$ (eq) | Temperature (°C.) | Reaction condition | |
| Method 1 | 10 | 2.0 | 1.3 | −78 | Adding PhNTf$_2$ into a mixture of the compound of formula (XI) and LiHMDS | 8.19 g (72%) |
| Method 2 | 10 | 2.0 | 1.3 | 0 | Adding the compound of formula (XI) into a mixture of LiHMDS and PhNTf$_2$ | 9.8 g (86.1%) |

As shown in Table 1, the yield of the compound of formula (IX) prepared according to Method 2 is higher than that of the compound of formula (IX) prepared according to Method 1.

<Step 2>

The compound of formula (IX) is prepared by subjecting the triflic enolate derivative of formula (X) obtained in Step 1 to a reaction with alkylsilylmethyl magnesium chloride or arylsilylmethyl magnesium chloride in the presence of a metallic catalyst.

Examples of the metallic catalyst used in the reaction include tetrakis(triphenylphosphine)palladium [Pd(PPh$_3$)$_4$] and the amount of the metallic catalyst used is preferably 0.01 to 0.1 molar equivalents based on the triflic enolate derivative of formula (X).

Examples of the alkylsilylmethyl magnesium chloride include (C$_1$ to C$_6$ alkyl)silylmethyl magnesium chloride such as trimethylsilylmethyl magnesium chloride and the like. Examples of the arylsilylmethyl magnesium chloride include t-butyldiphenylsilylmethyl magnesium chloride and the like. The amount of the alkylsilylmethyl magnesium chloride or arylsilylmethyl magnesium chloride used above is preferably 1 to 2 molar equivalents based on the triflic enolate derivative of formula (X). The alkylsilylmethyl magnesium chloride or arylsilylmethyl magnesium chloride can be prepared by one of the conventional method comprising the step of treating magnesium with (chloromethyl)alkylsilane or (chloromethyl)arylsilane.

The reaction may be conducted in an organic solvent at 0° C. to 20° C., preferably 5° C. to 10° C., for 1 to 3 hrs, and examples of the organic solvent include, but are not limited to, ether such as diethylether or tetrahydrofuran; chloroalkane such as methylene chloride; and a mixture thereof.

In order to obtain a crystalline form of the cycloalkene compound of formula (IX), the inventive method for preparing entecavir can further comprise the step of inducing the crystallization of the compound of formula (IX) by using a mixture of isopropyl alcohol and water.

According to the above method, the compound of formula (IX) can be prepared in a high yield of 86% or more.

<Step 3>

The epoxide derivative of formula (VIII) is prepared by treating the compound of formula (IX) obtained in step 2 with peroxide.

Examples of peroxide include m-chloroperoxybenzoic acid, hydrogen peroxide, t-butyl hydroperoxide (TBHP), osmium tetroxide(OsO$_4$), sodium periodate, and a mixture thereof. The amount of the peroxide used is preferably 1 to 3 molar equivalents based on the compound of formula (IX).

The reaction may be conducted in an organic solvent at 0° C. to 25° C. preferably 10° C. to 25° C., for 1 to 3 hrs, and examples of the organic solvent include, but are not limited to, C$_1$ to C$_6$ alcohol such as methanol, ethanol, isopropanol, or t-butanol; nitrile such as acetonitrile; chloroalkane such as methylene chloride; and a mixture thereof.

According to the above method, the epoxide derivative of formula (VIII) can be prepared in a form of crystalline solid.

<Step 4>

The β-exomethylene compound of formula (VII) is prepared by hydrolyzing the epoxide derivative of formula (VIII) obtained in Step 3.

The hydrolysis may be conducted in an organic solvent at 0° C. to 30° C., and examples of the organic solvent include, but are not limited to, chloroalkane such as methylene chloride; C$_1$ to C$_6$ alcohol such as methanol; and a mixture thereof.

According to the above method, the β-exomethylene compound of formula (VII) can be prepared in a high yield of 75% through 5 steps from the cyclopentanol compound of formula (XIII).

<Step 5>

The α-exomethylene derivative of formula (II) is prepared by carrying out a Mitsunobu reaction of the β-exomethylene compound of formula (VII) obtained in Step 4 with triphenylphosphine and di(C$_1$ to C$_6$ alkyl)azodicarboxylate.

The amount of the triphenylphosphine used above is preferably 1 to 2 molar equivalents based on the β-exomethylene compound of formula (VII).

Examples of di(C$_1$ to C$_6$ alkyl)azodicarboxylate include diisopropylazodicarboxylate (DIAD), diethylazodicarboxylate (DEAD), and a mixture thereof and the amount of the di(C$_1$ to C$_6$ alkyl)azodicarboxylate used above is preferably 1 to 2 molar equivalents based on the β-exomethylene compound of formula (VII).

The additive selected from the group consisting of benzoic acid, 4-phenylbenzoic acid, p-nitrobenzoic acid, p-methoxybenzoic acid, and a mixture thereof may be used in the above reaction and the amount of the additive is preferably 1 to 2 molar equivalents based on the β-exomethylene compound of formula (VII).

The reaction may be conducted in an organic solvent at 0° C. to 25° C., preferably 0° C. to 5° C., for 30 min to 2 hrs, and examples of the organic solvent include, but are not limited to, tetrahydrofuran, methylene chloride; and a mixture thereof.

The reaction may be carried out according to Method 1 which comprises the steps of adding the DIAD into a triphenylphosphine solution in the organic solvent to obtain a suspension, and adding a mixture solution of the β-exomethylene compound of formula (VII) and benzoic acid in tetrahydrofuran to the suspension; or Method 2 which comprises the step of adding DIAD to a mixture of the β-exomethylene compound of formula (VII), triphenylphosphine, and benzoic acid dropwise.

The yield of the compound of formula (II) prepared according to Method 2 is 70% which is higher than that of the compound of formula (II) prepared according to Method 1 (yield: 68.6%). Further, Method 2 is required one reactor so as to be useful in mass production of entecavir.

<Step 6>

The compound of formula (III) is prepared by hydrolyzing the compound of formula (II) obtained in Step 5 in a basic solution to remove the benzoyl of the compound of formula (II).

Examples of the base used to form the basic solution include, but are not limited to, sodium hydroxide, potassium hydroxide, ammonium hydroxide, and a mixture thereof, and the amount of the base used above is preferably 1 to 2 molar equivalents based on the compound of formula (II).

The hydrolysis may be conducted in an organic solvent at −5° C. to room temperature, preferably 0° C. to 5° C., for 30 min to 5 hrs, and examples of the organic solvent include, but are not limited to, tetrahydrofuran, methylene chloride, and a mixture thereof.

<Step 7>

The nucleoside compound of formula (V) is prepared by conducting a Mitsunobu reaction of the compound of formula (III) obtained in Step 6 with a purine derivative of formula (IV).

Examples of the purine derivative of formula (IV) include 2-amino-6-halopurine such as 2-amino-6-chloropurine; and 6-O-benzylguanine, and the amount of the purine derivative of formula (IV) used above is preferably 1 to 2 molar equivalents based on the compound of formula (III).

The Mitsunobu reaction may be conducted in an organic solvent in the presence of triphenylphosphine and di($C_1$ to $C_6$ alkyl)azodicarboxylate at 0° C. to 25° C., preferably 0° C. to 5° C., for 30 min to 2 hrs.

The amount of triphenylphosphine is preferably 1 to 2 molar equivalents based on the compound of formula (III).

Examples of the di($C_1$ to $C_6$ alkyl)azodicarboxylate include diisopropylazodicarboxylate (DIAD), diethylazodicarboxylate (DEAD), and a mixture thereof, and the amount of the di($C_1$ to $C_6$ alkyl)azodicarboxylate is preferably 1 to 2 molar equivalents based on the compound of formula (III).

Examples of the organic solvent include, but are not limited to, tetrahydrofuran, methylene chloride, and a mixture thereof.

The nucleoside compound of formula (V) according to the above method can be prepared in high yield of 64.7% as a solid.

<Step 8>

The compound of formula (VI) is prepared by subjecting the nucleoside compound of formula (V) obtained in Step 7 to a reaction with tetrabutyl ammonium fluoride (TBAF) to remove the protecting group $R_2$.

The amount of tetrabutyl ammonium fluoride used is preferably 1 to 2 molar equivalents based on the nucleoside compound of formula (V).

The reaction may be conducted in an organic solvent at 20° C. to 30° C., preferably 20° C. to 25° C., for 1 to 5 hrs and examples of the organic solvent include tetrahydrofuran, methylene chloride, and a mixture thereof.

<Step 9>

The entecavir compound of formula (I) is prepared by hydrolyzing the compound of formula (VI) obtained in Step 8.

The hydrolysis is conducted by heating the compound of formula (VI) in an acidic solution to remove the protecting group $R_1$ and X.

The acidic solution used above may be prepared by dissolving an acid selected from the group consisting of hydrochloric acid, sulfuric acid, trifluoroacetic acid, and a mixture thereof in water. It is preferable to use 2N hydrochloric acid solution as an acidic solution in an amount of 10 to 20 times by weight based on the compound of formula (VI).

The reaction may be conducted at 60° C. to 90° C., preferably 80° C. to 85° C., for 3 to 6 hrs.

After de-protection of the compound of formula (VI) in the acidic solution, a neutralization of the resulting solution to pH 6 to 8 may be further conducted by using sodium hydroxide solution.

The compound of formula (XI) which is used as a starting material in the inventive method, may be prepared by one of the conventional method well-known in the art (see Korean Patent Publication No. 2010-0076640), preferably by a preparation method as shown in Reaction Scheme 6.

Reaction Scheme 6

(XII)                (XIII)

(XI)

wherein $R_1$ and $R_2$ are the same as defined above.

Specifically, the cyclopentanol compound is prepared as a crystalline solid by a preparation process comprising the steps of: treating the cyclopentene derivative of formula (XII) with (+)-diisopinocampheyl borane ((+)-$Ipc_2BH$) and $H_2O_2$; extracting the resulting mixture (which comprises the cyclopentanol compound of formula (XIII) and isopinocampheol as a by-product) with a hydrocarbon-based solvent (e.g., heptane, hexane or octane) to induce the separation of an organic layer; washing the separated organic layer with a mixture of water and alcohol (e.g., methanol) to remove isopinocampheol selectively; and inducing the crystallization of the compound of formula (XIII) by adding a solvent as a crystallization aid.

The amount of (+)-$Ipc_2BH$ and $H_2O_2$ are preferably 1 to 3 mole equivalents and 1 to 7 mole equivalent, respectively, based on the cyclopentene derivative of formula (XII).

The washing process may be conducted twice or more, preferably three times or more by using a mixture of water and alcohol mixed in a weight ratio ranging from 1:1 to 1:3. More preferably, the washing process may be conducted five times by using any of the mixtures of water and alcohol having a mix weight ratio of 1:1, 1:1.5, 1:2, 1:2.5, and 1:3.

Examples of the solvent for crystallization include hydrocarbon-based solvent such as hexane, heptane or octane; alcohol such as methanol, ethanol or isopropyl alcohol; water; and a mixture thereof.

The reaction may be conducted in an organic solvent at 0° C. to 40° C.

Next, the compound of formula (XI) is prepared by conducting oxidation of the cyclopentanol compound of formula (XIII) with a mixture of pyridine.SO$_3$ complex, trialkylamine, and dimethylsulfoxide, wherein the pyridine.SO$_3$ complex is superior to the dess martin periodinane (DMP) in its low price and stability. The compound of formula (XI) thus obtained can be used without further purification.

The amount of pyridine.SO$_3$ complex, trialkylamine, and dimethylsulfoxide are 1 to 3 mole equivalents, 1 to 4 mole equivalents and 1 to 10 mole equivalents respectively, based on the cyclopentanol compound of formula (XIII).

The reaction may be conducted in an organic solvent at 0° C. to room temperature.

In accordance with another aspect of the present invention, there are provided the α-exomethylene derivative of formula (II), the β-exomethylene derivative of formula (VII), the epoxide derivative of formula (VIII), the cycloalkene compound of formula (IX), the triflic enolate derivative of formula (X), and the crystalline cyclopentanol compound of formula (XIII), which are used in the preparation of entecavir of formula (I) or a solvate thereof as an intermediate.

In accordance with further aspect of the present invention, there are provided a method for preparing a solvate of crystalline entecavir dimethylformamide of formula (XIV), comprising the steps of: dissolving the entecavir compound of formula (I) in a solvent containing dimethyl formamide; and inducing the crystallization of the compound of formula (XIV) therefrom; and optionally filtering and drying; and the solvate of crystalline entecavir dimethylformamide of formula (XIV) prepared by the method:

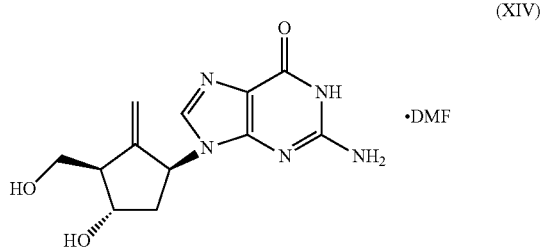

(XIV)

wherein DMF is dimethylformamide.

The DMF is comprised in an amount of 10 to 40 weight % based on the total weight of the solvate.

Preferably, the dry process may be conducted under nitrogen atmosphere to obtain a stable DMF monosolvate.

The solvate shows peaks having a peak intensity of 10% or more at diffraction angles (2θ±0.2) of 10.2, 14.4, 14.5, 16.6, 17.9, 18.8, 19.3, 19.8, 21.4, 21.9, 24.5, 25.5, 25.8, 26.7, 29.3, and 30.2, as shown in FIG. 1, in a X-ray diffraction spectrum obtained using Cu-Kα radiation.

Further, the solvate can be used as an intermediate for preparing the inventive entecavir. Specifically, the inventive entecavir is prepared by a conventional re-crystallization method comprising the steps of: dissolving the solvate in a solvent such as water; and cooling the resulting solution to precipitate entecavir.

In accordance with the inventive method for preparing entecavir using the novel intermediates, a high-purity entecavir can be prepared economically in a high yield.

The following examples illustrate the embodiments of the present invention in more detail. However, the following examples of the present invention are merely examples, and the present invention is not limited thereto.

Example 1-1

Preparation of trifluoromethanesulfonic acid 4-(t-butyl-diphenyl-silanyloxy)-5-trityloxymethyl-1-cyclopentenyl ester (compound of formula (X))

3-(t-Butyl-diphenyl-silanyloxy)-2-trityloxymethyl-cyclopentanone (31 g, 50.7 mmol) was dissolved in anhydrous tetrahydrofuran (310 ml) and cooled to −78° C. Lithium hexamethyldisilazane (17.0 g, 101.5 mmol) was added thereto and stirred at −78° C. for 1 hr. To the mixture thus obtained, N-phenyltrifimide (23.6 g, 66 mmol) was added and heated to room temperature, followed by stirring at room temperature overnight. After completion of the reaction, saturated sodium bicarbonate (310 ml) was added thereto. The resulting solution was extracted with ethyl acetate (310 ml), dried over anhydrous sodium sulfate, filtered, and condensed under a reduced pressure. The material thus obtained was purified with column chromatography to obtain the title compound (33.5 g, yield: 88.9%).

NMR (300 MHz, CDCl$_3$): δ 7.36 (m, 4H), 7.09-6.99 (m, 21H), 5.50 (s, 1H), 4.14 (d, 1H), 2.89 (dd, 1H), 2.68 (s, 1H), 2.59 (dd, 1H), 2.37-2.34 (m, 1H), 2.15 (d, 1H), 0.80 (s, 9H)

Example 1-2

Preparation of t-butyl-diphenyl-(3-trimethylsilylmethyl-2-trityloxymethyl-cyclopenten-3-yloxy)-silane (compound of formula (IX))

The enolate compound of formula (X) obtained in Example 1-1 (33.5 g, 45.1 mmol) was dissolved in diethylether (335 ml). Tetrakis(triphenylphosphine)palladium (2.6 g, 2.25 mmol) was added thereto at room temperature and cooled to 0° C. To the resulting mixture, 1 M trimethylsilyl magnesium chloride (90.2 ml, 90.2 mmol) was added and stirred at room temperature for 1 hr. After completion of the reaction, the resulting mixture was cooled to 0° C. The cooled mixture was quenched with saturated sodium bicarbonate (335 ml) and filtered through Celite. The resulting solid was washed with ethyl acetate, dried over anhydrous sodium sulfate, filtered, and condensed under a reduced pressure. The material thus obtained was purified with column chromatography to obtain the title compound (26.99 g, yield: 87.4%).

NMR (300 MHz, CDCl$_3$): δ 7.59 (dd, 4H), 7.33-7.14 (m, 21H), 5.06 (s, 1H), 4.33 (d, 1H), 2.90 (dd, 1H), 2.78-2.73 (m, 1H), 2.64-2.62 (m, 1H), 2.26-2.24 (m, 1H), 2.09 (d, 1H), 1.50 (d, 1H), 1.23 (d, 1H), 1.00 (s, 9H), 0.01 (s, 9H)

Example 1-3

Preparation of 3-(t-butyl-diphenyl-silanyloxy)-1-trimethylsilanylmethyl-2-trityloxymethyl-6-oxa-bicyclo[3.1.0]hexane (compound of formula (VIII)

The compound of formula (IX) obtained in Example 1-2 (708 g, 1.03 mol) was dissolved in isopropyl alcohol (16 L) and cooled to 0° C. To the resulting solution, sodium phosphate (2214 g, 15.59 mol) and 77% m-chloroperoxybenzoic acid (699 g, 3.11 mol) was added successively. The resulting mixture was stirred at 0° C. for 2 hrs. The solid was filtered to obtain the solid mixture of the title compound and sodium phosphate (724 g).

NMR (300 MHz, $CD_2Cl_2+D_2O$): δ 7.65-7.22 (m, 25H), 4.74 (t, 2H), 3.44 (q, 1H), 3.27 (dd, 1H), 3.13 (s, 1H), 2.88 (t, 1H), 2.42-2.41 (m, 1H), 1.99-1.88 (m, 2H), 1.02-0.93 (m, 9H), 0.15-0.13 (m, 9H)

Example 1-4

Preparation of 1-(S)-4-(t-butyl-diphenyl-silanyloxy)-2-methylene-3-trityloxymethyl cyclopentanol (compound of formula (VII))

A solid mixture of the compound of formula (VIII) obtained in Example 1-3 and sodium phosphate (724 g) was added to methanol (10 L) and stirred at room temperature. 77% m-chloroperoxybenzoic acid (350 g, 1.56 mol) and methylene chloride (5 L) was added thereto to complete the reaction. The resulting mixture was quenched by adding a mixture of 20% aqueous sodium bisulfate (1.5 L) and 12% aqueous sodium bicarbonate (1.5 L). The reaction mixture thus obtained was extracted with methylene chloride (1.6 L) twice and dried over sodium sulfate, filtered, and condensed under a reduced pressure to obtain the title compound (494 g, yield of the title compound obtained from the compound of formula (XI): 60.5%).

NMR (300 MHz, $CDCl_3$): δ 7.84-7.58 (m, 5H), 7.33-7.18 (m, 39H), 5.40 (s, 0.2H), 5.18 (s, 1H), 5.11 (s, 0.2H), 4.99 (s, 1H), 4.65 (d, 1H), 4.13 (q, 2H), 3.02 (m, 3H), 2.87 (m, 2H), 1.88 (d, 1H), 1.00 (s, 17H)

Example 1-5

1-benzoyl-4-(t-butyl-diphenyl-silanyloxy)-2-methylene-3-trityloxymethyl-cyclopentane (compound of formula (II))

Triphenylphosphine (311 g, 1.18 mol) was dissolved in tetrahydrofuran (4.9 L) and cooled to 0° C. To the solution thus obtained, diisopropylazodicarboxylate (DIAD) (233 ml, 1.18 mol) was added and stirred at 0° C. for 1 hr to obtain a suspension. Tetrahydrofuran (4.9 L) was added to a mixture of the compound of formula (VII) obtained in Example 1-4 (494 g, 0.79 mol) and benzoic acid (145 g, 1.18 mol). The suspension of triphenylphosphine and DIAD was added thereto at 0° C. and stirred at the same temperature for 0.5 hrs. The mixture thus obtained was condensed under a reduced pressure to remove the solvent and ethyl acetate (4.9 L) was added thereto, followed by washing with 0.5 N aqueous sodium hydroxide. To the resulting material sodium sulfate was added, filtered, and condensed under a reduced pressure. The resulting material was crystallized by adding methanol (4.9 L) and filtered to obtain the title compound (369 g, yield: 68.6%).

NMR (300 MHz, $CDCl_3$): δ 8.09 (dd, 2H), 7.56 (dd, 5H), 7.33-7.20 (m, 23H), 5.60 (t, 1H), 5.26 (d, 2H), 4.11 (q, 1H), 3.13-3.08 (m, 1H), 3.02 (d, 1H), 2.85 (q, 1H), 2.24-2.18 (m, 1H), 1.94-1.88 (m, 1H), 1.54 (s, 3H), 0.99 (s, 9H)

Example 1-6

Preparation of 1-(R)-4-(t-butyl-diphenyl-silanyloxy)-2-methylene-3-trityloxymethyl cyclopentanol (compound of formula (III))

The compound of formula (II) obtained in Example 1-5 (367 g, 0.5 mol) was mixed with 1% sodium hydroxide solution in methanol (7.34 L) and methylene chloride (3.7 L) at room temperature for 5 hrs. After completion of the reaction, water (7.3 L) was added to the resulting mixture to separate an aqueous layer. The separated aqueous layer was extracted with methylene chloride (7.3 L). To the resulting material, sodium sulfate was added, dried and filtered to obtain the title compound (404 g, yield: >100%).

NMR (300 MHz, $CDCl_3$): δ 7.65-7.60 (m, 4H), 7.39-7.17 (m, 21H), 5.35 (s, 1H), 5.10 (s, 1H), 4.30 (d, 1H), 2.97 (s, 1H), 2.88-2.79 (m, 2H), 2.73 (d, 1H), 1.78 (t, 2H), 1.02 (s, 9H)

Example 1-7

Preparation of 9-[4-(t-butyl-diphenyl-silanyloxy)-2-methylene-3-trityloxymethyl-cyclopentyl]-6-chloro-9H-purin-2-yl amine (compound of formula (V))

Triphenylphosphine (13.37 g, 50.88 mmol) was dissolved in tetrahydrofuran (240 ml) and cooled to 0□. Diethylazodicarboxylate (DEAD) (8.3 ml, 50.88 mmol) was added thereto and stirred at 0° C. for 1 hr to obtain a suspension. Tetrahydrofuran (160 ml) was added to a mixture of the compound of formula (III) obtained in Example 1-6 (15.93 g, 25.44 mmol) and 2-amino-6-chloropurin (8.64 g, 50.88 mmol) and the suspension of triphenylphosphine and DEAD was added thereto at 0° C., followed by stirring at the same temperature for 1 hr. After completion of the reaction, ethyl acetate (400 ml) was added to the resulting mixture and washed with 0.5 N aqueous sodium hydroxide (400 ml) at 0° C. three times. The resulting material was dried over anhydrous sodium sulfate, filtered, condensed under a reduced pressure, and purified with column chromatography to obtain the title compound (12.8 g, yield: 64.7%).

NMR (300 MHz, DMSO-$d_6$): δ 7.82 (s, 1H), 7.61 (d, 4H), 7.49-7.20 (m, 21H), 6.69 (br s, 2H), 5.53 (t, 1H), 4.91 (s, 1H), 4.57 (s, 1H), 4.40 (s, 1H), 3.19-3.13 (m, 1H), 3.08-3.03 (m, 1H), 2.83 (s, 1H), 2.13-2.10 (m, 2H), 1.03 (s, 9H)

Example 1-8

Preparation of 4-(2-amino-6-chloro-4,5-dihydropurin-9-yl)-3-methylene-2-trityloxymethyl-cyclopentanol (compound of formula (VI))

The compound of formula (V) obtained in Example 1-7 (3.2 g, 4.12 mmol) was dissolved in anhydrous tetrahydrofuran (32 ml). To the resulting solution, 1 M tetrabutyl ammonium fluoride solution in tetrahydrofuran (8.24 mL, 8.24 mmol) was added and stirred at room temperature for 13 hrs. After completion of the reaction, the resulting mixture was quenched by adding distilled water (30 ml). The solution thus obtained was extracted with ethyl acetate (30 ml), dried over anhydrous sodium sulfate, filtered, and condensed. The resulting material was stirred in methanol (32 ml) to obtain the title compound (1.6 g, yield: 71.6%).

NMR (300 MHz, DMSO-$d_6$): δ 8.19 (s, 1H), 7.98-7.25 (m, 15H), 6.84 (s, 2H), 5.44 (t, 1H), 5.07 (d, 1H), 4.88 (s, 1H), 4.54 (s, 1H), 4.25 (s, 1H), 3.30-3.17 (m, 2H), 2.64 (s, 1H), 2.26-2.08 (m, 2H)

Example 1-9

Preparation of 2-amino-9-(4-hydroxy-3-hydroxymethyl-2-methylene-cyclopentyl)-1,9-dihydropurin-6-one (entecavir of formula (I))

Acetonitril (30 ml) and 2N aqueous hydrochloric acid (23.3 ml) were added to the compound of formula (VI)

obtained in Example 1-8 (1.38 g, 2.56 mmol) and stirred at 82° C. for 12 hrs with heating. After completion of the reaction, the resulting mixture was cooled to room temperature and washed with ethyl acetate to remove tritylcarbinol. The material thus obtained was neutralized to pH 6.8 by using 3N aqueous sodium hydroxide (13.6 ml) and stirred at 90° C. for 1 hr. The solution thus obtained was stirred with cooling slowly to room temperature and further stirred at room temperature for 1 hr to obtain crystal. The resulting material was cooled to 6° C. and stirred for 1 hr to obtain the title compound (0.554 g, yield: 73.1%).

NMR (300 MHz, MeOH-$d_4$): 10.6 (s, 1H), 7.78 (s, 1H), 5.53 (t, 1H), 5.26 (t, 1H), 4.82 (t, 1H), 4.43-4.40 (m, 1H), 3.81 (d, 2H), 2.70 (s, 1H), 2.47-2.38 (m, 1H), 2.27-2.20 (m, 1H)

Example 1-10

Preparation of the solvate of 2-amino-9-(4-hydroxy-3-hydroxymethyl-2-methylene-cyclopentyl)-1,9-dihydro-purin-6-one N,N-dimethylformamide (compound of formula (XIV))

The compound obtained in Example 1-9 (1 g) was added to N,N-dimethylformamide (5 ml) and stirred at room temperature for 2 hrs and at 0° C. for 1 hr. The resulting solution was filtered to obtain the title compound as a white-colored solid (0.95 g, yield: 85.6%).

NMR (300 MHz, MeOH-$d_4$): 10.6 (s, 1H), 7.95 (s, 1H), 7.67 (s, 1H), 5.36 (t, 1H), 5.10 (t, 1H), 4.87 (d, 1H), 4.83 (t, 1H), 4.56 (t, 1H), 4.24 (s, 1H), 3.54 (t, 2H), 2.89 (s, 3H), 2.72 (s, 3H), 2.50 (m, 1H), 2.21 (m, 1H), 2.04 (m, 1H)

Example 1-11

Preparation of a high purity of 2-amino-9-(4-hydroxy-3-hydroxymethyl-2-methylene-cyclopentyl)-1,9-dihydro-purin-6-one monohydrate (compound of formula (I))

The compound of formula (XIV) obtained in Example 1-10 (1.1 g) was mixed with distilled water (16.5 ml) and stirred at 95° C. for 1 hr. The resulting solution was cooled to room temperature to crystallize and stirred at 10° C. for 1 hr. The resulting solid was filtered and dried under a nitrogen atmosphere to obtain the title compound with a purity of 99.8% or more as a white-colored solid (0.9 g, yield: 96.9%).

Example 2-1

Preparation of 3-(t-butyl-diphenyl-silanyloxy)-2-trityloxymethyl-cyclopentanol (compound of formula (XIII))

The 2M $BH_3$.DMS solution in tetrahydrofuran (210 ml, 0.924 mol) was mixed with anhydrous tetrahydrofuran (300 ml) in a reactor under a nitrogen stream and cooled to 5° C. (−)-α-pinene (155 ml, 0.924 mol) was added thereto dropwise for 0.5 hrs. The solid phase of (+)-$Ipc_2BH$ thus obtained was heated to 35° C. and t-butyl-diphenyl-(2-trityloxymethyl-cyclo-2-pentenyloxy)-silane of formula (II) (100 g) was added thereto. The resulting mixture was stirred for 3 hrs and 3 N aqueous sodium hydroxide (196 ml) was added thereto dropwise for 1 hr with maintaining the temperature of 0° C. to 10° C. To the resulting mixture, hydrogen peroxide (105 ml) was added dropwise for 1 hr or more and stirred for 1 hr. To the resulting reaction mixture, a mixture solution of 10% $NaHSO_3$ (250 ml) and 8% $NaHCO_3$ (250 ml) was added thereto dropwise to remove the excess hydrogen peroxide. The resulting material was extracted with heptane (500 ml) to separate an organic layer. The separated organic layer was washed five times using mixtures of water and methanol mixed in a weight ratio of 1:1, 1:1.5, 1:2, 1:2.5 or 1:3 to remove isopinocampheol. The resulting solution was condensed under a reduced pressure, crystallized with heptane (300 ml), and filtered at 0° C. to obtain the title compound as a crystal (67 g, yield: 65%).

NMR (300 MHz, $CDCl_3$): δ 7.57-7.21 (m, 25H), 3.91-3.81 (m, 2H), 3.12 (dd, 1H), 2.74 (br, 1H), 2.68 (t, 1H), 2.34 (m, 1H), 1.77-1.72 (m, 3H), 1.53-1.48 (m, 1H), 1.01 (s, 9H)

m.p.: 95.6° C. to 97° C.

Example 2-2

Preparation of 3-(t-butyl-diphenyl-silanyloxy)-2-trityloxymethyl-cyclopentanone (compound of formula (XI))

The compound of formula (XIII) obtained in Example 2-1 (60 g, 97.9 mmol) was mixed with DMSO (36 ml) and methylene chloride (300 ml). The resulting solution was cooled to 0° C. and N,N-diisopropylethylamine (DIPEA) (59.7 ml, 0.343 mol) was added thereto, followed by adding a mixture solution of pyridine.$SO_3$ complex (31.2 g), pyridine (15.9 ml) and DMSO (36 ml). The mixture thus obtained was stirred for 30 min. After completion of the reaction, the organic layer thus obtained was washed with saturated ammonium chloride (300 ml), 2M HCl solution (300 ml), sodium bicarbonate solution (300 ml) and brine (300 ml) respectively, dried over anhydrous sodium sulfate, filtered, and condensed under a reduced pressure to obtain the title compound (60 g, yield: 99%).

NMR (300 MHz, $CDCl_3$): δ 7.62-7.18 (m, 25H), 4.53 (q, 1H), 3.34 (dd, 1H), 3.02 (dd, 1H), 2.53 (m, 1H), 2.32 (q, 1H), 2.18 (m, 1H), 1.99-1.88 (m, 2H), 0.89 (9H)

Example 2-3

Preparation of trifluoromethanesulfonic acid 4-(t-butyl-diphenyl-silanyloxy)-5-trityloxymethyl-1-cyclopentenyl ester (compound of formula (X))

1M lithium hexamethyldisilazane solution in tetrahydrofuran (2.62 L, 2.62 mol) was cooled to 0° C. in a reactor. A mixture solution of N-phenyltriflimide (608.4 g, 1.70 mol) and anhydrous tetrahydrofuran (2.4 L) was added to the solution for 1 hr, followed by adding a mixture of the compound of formula (XI) obtained in Example 2-2 (800 g, 1.31 mol) and anhydrous tetrahydrofuran (2.4 L) for 1 to 1.5 hrs. The resulting mixture was stirred at 0° C. for 1 hr. After completion of the reaction, 3% aqueous sodium bicarbonate (8 L) was added to the mixture and extracted with ethyl acetate (8 L). The organic layer thus separated was dried over anhydrous sodium sulfate, filtered, and condensed under a reduced pressure. The residue thus obtained was mixed with heptane (6 L) and Celite (800 g) and stirred at room temperature for 2 hrs. The resulting mixture was filtered through Celite to remove alien substance. The organic layer thus obtained was washed with a mixture of methanol and water mixed in a weight ratio of 6:1 (5.6 L) twice, dried over anhydrous sodium sulfate, filtered, and condensed under a reduced pressure to obtain the title compound (892 g).

NMR (300 MHz, $CDCl_3$): δ 7.36 (m, 4H), 7.09-6.99 (m, 21H), 5.50 (s, 1H), 4.14 (d, 1H), 2.89 (dd, 1H), 2.68 (s, 1H), 2.59 (dd, 1H), 2.37-2.34 (m, 1H), 2.15 (d, 1H), 0.80 (s, 9H)

Example 2-4

Preparation of t-butyl-diphenyl-(3-trimethylsilylmethyl-2-trityloxymethyl-cyclopenten-3-yloxy)-silane (compound of formula (IX))

Magnesium (turning) (33 g, 5.22 mol) was mixed with anhydrous tetrahydrofuran (2 L). 1,2-Dibromoethane (8 ml) was added thereto and stirred for 15 min. To the resulting solution, a mixture of chloromethyltrimethylsilane (364 ml, 2.61 mol) and anhydrous tetrahydrofuran (0.6 L) was added dropwise for 10 min. The mixture solution thus obtained was heated to 40° C. and cooled slowly to precipitate trimethylsilylmethyl magnesium chloride. A mixture of the compound of formula (X) obtained in Example 2-3 (892 g), tetrakis (triphenylphosphine)palladium (37.7 g, 0.033 mmol) and anhydrous tetrahydrofuran (4.5 L) were added to the resulting solution for 20 min dropwise and stirred at room temperature for 1 to 2 hrs. After completion of the reaction, the resulting solution was cooled to 0° C. and 3% aqueous sodium bisulfonate (8 L) was added thereto. The resulting mixture was filtered through Celite, washed with ethyl acetate (4 L). The organic layer thus separated was condensed under a reduced pressure. The residue thus obtained was mixed with heptane (6 L) and Celite (400 g), stirred for 2 hrs, filtered and washed with heptane (2 L). The organic layer thus separated was washed with a mixture of methanol and water mixed in a weight ratio of 6:1 (5.6 L) twice, dried over anhydrous sodium sulfate, filtered, and condensed under a reduced pressure. The residue was crystallized with a mixture of isopropyl alcohol and water to obtain the title compound as a crystalline solid (786 g).

NMR (300 MHz, CDCl$_3$): δ 7.59 (dd, 4H), 7.33-7.14 (m, 21H), 5.06 (s, 1H), 4.33 (d, 1H), 2.90 (dd, 1H), 2.78-2.73 (m, 1H), 2.64-2.62 (m, 1H), 2.26-2.24 (m, 1H), 2.09 (d, 1H), 1.50 (d, 1H), 1.23 (d, 1H), 1.00 (s, 9H), 0.01 (s, 9H)

m.p.: 57.8° C. to 59.0° C.

Example 2-5

Preparation of 3-(t-butyl-diphenyl-silanyloxy)-1-trimethylsilanylmethyl-2-trityloxymethyl-6-oxa-bicyclo[3.1.0]hexane (compound of formula (XIII))

The compound of formula (IX) obtained in Example 2-4 (786 g, 1.14 mol) was dissolved in isopropyl alcohol (12 L) and cooled to 0° C. Sodium phosphate (2.78 kg, 19.58 mol) and 77% m-chloroperoxybenzoic acid (292.5 g, 1.31 mol) were successively added thereto and stirred for 2.5 hrs. The solid thus obtained was filtered to obtain a mixture of the title compound and sodium phosphate (3.25 kg).

NMR (300 MHz, CD$_2$Cl$_2$+D$_2$O): δ 7.65-7.22 (m, 25H), 4.74 (t, 2H), 3.44 (q, 1H), 3.27 (dd, 1H), 3.13 (s, 1H), 2.88 (t, 1H), 2.42-2.41 (m, 1H), 1.99-1.88 (m, 2H), 1.02-0.93 (m, 9H), 0.15-0.13 (m, 9H)

Example 2-6

Preparation of 1-(S)-4-(t-butyl-diphenyl-silanyloxy)-2-methylene-3-trityloxymethylcyclopentanol (compound of formula (VII))

A mixture (3.25 kg) of the compound of formula (XIII) obtained in Example 2-5 and sodium phosphate was mixed with methanol (8 L) and methylene chloride (4 L). 77% m-Chloroperoxybenzoic acid (292.5 g) was added thereto and stirred for 1 to 1.5 hrs. After completion of the reaction, the resulting mixture was filtered to remove sodium phosphate and the solid thus obtained was washed with methylene chloride (4 L). To the material thus obtained, a mixture solution of 20% aqueous sodium bisulfate (2.4 L) and 6% sodium bicarbonate solution (4.8 L) was added and cooled quickly. The organic layer thus obtained was separated and the aqueous layer was extracted with methylene chloride (4 L). The organic layer thus separated was combined, dried over with sodium sulfate, filtered, and condensed under a reduced pressure to obtain the title compound (587.3 g, yield of the compound of formula (VII) obtained from compound of formula (III): 72%).

NMR (300 MHz, CDCl$_3$): δ 7.84-7.58 (m, 5H), 7.33-7.18 (m, 39H), 5.40 (s, 0.2H), 5.18 (s, 1H), 5.11 (s, 0.2H), 4.99 (s, 1H), 4.65 (d, 1H), 4.13 (q, 2H), 3.02 (m, 3H), 2.87 (m, 2H), 1.88 (d, 1H), 1.00 (s, 17H)

Example 2-7

Preparation of 1-benzoyl-4-(t-butyl-diphenyl-silanyloxy)-2-methylene-3-trityloxymethyl-cyclopentane (compound of formula (II))

The compound of formula (VII) obtained in Example 3-6 (500 g, 0.8 mol), triphenyl phosphine (314.8 g, 1.2 mol) and benzoic acid (146.7 g, 1.2 mol) was mixed in tetrahydrofuran (10 L) and cooled to 0° C. DIAD (242.7 ml, 1.2 mol) was added thereto dropwise and stirred at 0° C. for 1 hr. After completion of the reaction, the resulting mixture was condensed under a reduced pressure to remove the solvent. Ethyl acetate (5 L) was added thereto and washed with 0.5 N aqueous sodium hydroxide (5 L). To the organic layer thus separated, sodium sulfate was added, dried, filtered, and condensed. The resulting material was dissolved in ethyl acetate (1 L) and methanol (4 L) was added to crystallize the title compound. The solid thus obtained was filtered to obtain the title compound as a solid (408.3 g, yield: 70.0%).

NMR (300 MHz, CDCl$_3$): δ 8.09 (dd, 2H), 7.56 (dd, 5H), 7.33-7.20 (m, 23H), 5.60 (t, 1H), 5.26 (d, 2H), 4.11 (q, 1H), 3.13-3.08 (m, 1H), 3.02 (d, 1H), 2.85 (q, 1H), 2.24-2.18 (m, 1H), 1.94-1.88 (m, 1H), 1.54 (s, 3H), 0.99 (s, 9H)

m.p.: 142.3° C. to 144° C.

Example 2-8

Preparation of 1-(R)-4-(t-butyl-diphenyl-silanyloxy)-2-methylene-3-trityloxymethylcyclopentanol (compound of formula (III))

Sodium hydroxide (80 g, 2 mol) was mixed with methanol (4.0 L) in a reactor. The compound of formula (II) obtained in Example 2-7 (400 g, 0.5487 mol) and methylene chloride (2.0 L) were added thereto and reacted at room temperature for 5 hrs. After completion of the reaction, the resulting mixture was washed with water (2 L). To the organic layer thus separated, sodium sulfate was added, dried, and filtered to obtain the title compound (341 g, yield: 99%).

NMR (300 MHz, CDCl$_3$): δ 7.65-7.60 (m, 4H), 7.39-7.17 (m, 21H), 5.35 (s, 1H), 5.10 (s, 1H), 4.30 (d, 1H), 2.97 (s, 1H), 2.88-2.79 (m, 2H), 2.73 (d, 1H), 1.78 (t, 2H), 1.02 (s, 9H)

Example 2-9

Preparation of 9-[4-(t-butyl-diphenyl-silanyloxy)-2-methylene-3-trityloxymethyl-cyclopentyl]-6-chloro-9H-purin-2-yl amine (compound of formula (V))

Triphenylphosphine (216 g, 0.823 mol) was dissolved in tetrahydrofuran (3.43 L) and cooled to 0° C. DEAD (130 ml, 0.823 mol) was added thereto and stirred at 0° C. for 1 hr to obtain a suspension. The suspension was added to a mixture solution of the compound of formula (III) obtained in Example 2-8 (341 g, 0.5487 mol) and 2-amino-6-chloropurin (140 g, 0.823 mol) in tetrahydrofuran (3.43 L) at 0° C. and stirred at same temperature for 1 hr. After completion of the reaction mixture, ethyl acetate (3.43 L) was added to the resulting mixture and washed with 0.5 N aqueous sodium hydroxide (3.43 L) at 0° C. The material thus obtained was dried over anhydrous sodium sulfate, filtered, and condensed under a reduced pressure to obtain the title compound (426 g, yield: 99%).

NMR (300 MHz, DMSO-$d_6$): δ 7.82 (s, 1H), 7.61 (d, 4H), 7.49-7.20 (m, 21H), 6.69 (br s, 2H), 5.53 (t, 1H), 4.91 (s, 1H), 4.57 (s, 1H), 4.40 (s, 1H), 3.19-3.13 (m, 1H), 3.08-3.03 (m, 1H), 2.83 (s, 1H), 2.13-2.10 (m, 2H), 1.03 (s, 9H)

Example 2-10

Preparation of 4-(2-amino-6-chloro-4,5-dihydro-purin-9-yl)-3-methylene-2-trityloxymethyl-cyclopentanol (compound of formula (VI))

1 M tetrabutyl ammonium fluoride solution in tetrahydrofuran (1.1 L, 1.10 mol) was added to a solution prepared by dissolving the compound of formula (V) obtained in Example 2-9 (426 g, 0.5487 mol) in anhydrous tetrahydrofuran (4 L) and stirred at room temperature for 13 hrs. After completion of the reaction, distilled water (2.0 L) was added to the resulting mixture and extracted with ethyl acetate (2.0 L) twice. The organic layer thus separated was dried over anhydrous sodium sulfate, filtered, and concentrated. The resulting material was stirred in methanol (4.0 L) to obtain the title compound (212.6 g, yield: 72%).

NMR (300 MHz, DMSO-$d_6$): δ 8.19 (s, 1H), 7.98-7.25 (m, 15H), 6.84 (s, 2H), 5.44 (t, 1H), 5.07 (d, 1H), 4.88 (s, 1H), 4.54 (s, 1H), 4.25 (s, 1H), 3.30-3.17 (m, 2H), 2.64 (s, 1H), 2.26-2.08 (m, 2H)

Example 2-11

Preparation of 2-amino-9-(4-hydroxy-3-hydroxymethyl-2-methylene-cyclopentyl)-1,9-dihydro-purin-6-one (entecavir of formula (I))

The compound of formula (VI) obtained in Example 2-10 (200 g, 0.372 mol) was mixed with acetonitrile (3 L) and 2 N aqueous hydrochloric acid (3 L) and stirred at 82° C. for 12 hrs with heating. After completion of the reaction, the resulting solution was cooled to room temperature and washed with ethyl acetate (3 L) to remove tritylcarbinol. The resulting material was neutralized to pH 7 using 3 N aqueous sodium hydroxide (1.2 L) and stirred at 90° C. for 1 hr to obtain a solution. The solution was cooled to room temperature slowly with stirring and stirred at room temperature for 1 hr to crystallize. The resulting material was cooled to 6° C. and stirred for 1 hr to obtain the title compound as a solid (80.2 g, yield: 73%).

NMR (300 MHz, MeOH-$d_4$): 10.6 (s, 1H), 7.78 (s, 1H), 5.53 (t, 1H), 5.26 (t, 1H), 4.82 (t, 1H), 4.43-4.40 (m, 1H), 3.81 (d, 2H), 2.70 (s, 1H), 2.47-2.38 (m, 1H), 2.27-2.20 (m, 1H)

While the invention has been described with respect to the above specific embodiments, it should be recognized that various modifications and changes may be made to the invention by those skilled in the art which also fall within the scope of the invention as defined by the appended claims.

What is claimed is:

1. A method for preparing entecavir of formula (I), comprising the steps of:
(a) hydrolyzing an α-exomethylene derivative of formula (II) to obtain a compound of formula (III);
(b) carrying out a Mitsunobu reaction of the compound of formula (III) with a purine derivative of formula (IV) to obtain a nucleoside compound of formula (V);
(c) subjecting the nucleoside compound of formula (V) to a reaction with tetrabutyl ammonium fluoride to obtain a compound of formula (VI); and
(d) hydrolyzing the compound of formula (VI):

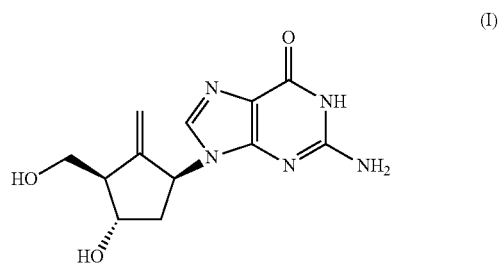

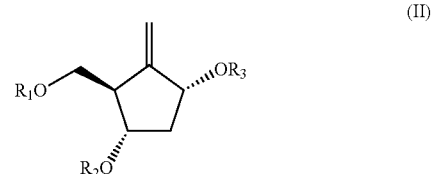

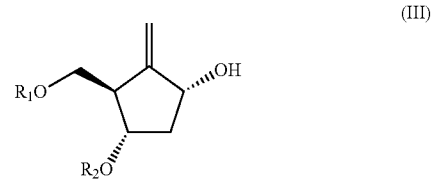

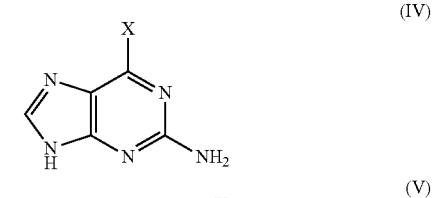

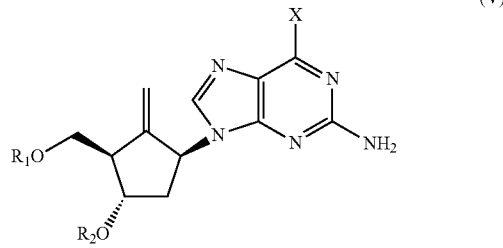

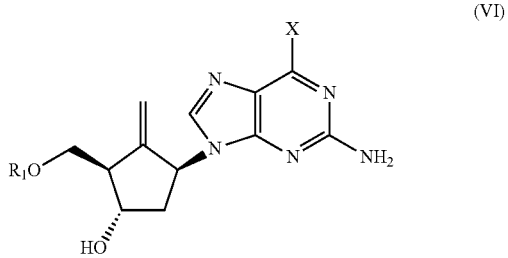

wherein

R$_1$ and R$_2$ are each independently a hydroxy-protecting group, or R$_1$ and R$_2$ are fused together to form a cyclic hydroxy-protecting group;

R$_3$ is benzoyl or arylbenzoyl; and

X is halogen or benzyloxy.

2. The method of claim 1, wherein the hydroxy-protecting group is selected from the group consisting of methyl having one, two, or three phenyl substituents; benzyl substituted with alkoxy or nitro; benzoyl; benzoyl substituted with alkoxy or nitro; silyl; silyl substituted with at least one substituent selected from the group consisting of alkyl and aryl; allyl; alkoxyalkyl; and tetrahydropyranyl.

3. The method of claim 1, wherein the cyclic hydroxy-protecting group is selected from the group consisting of benzylidene, naphthylidene, 4-phenylbenzylidene, cyclic acetal, cyclic ketal, cyclic carbonate, cyclic orthoester, and cyclic 1,3-(1,1,3,3-tetraisopropyl)disiloxanediyl.

4. The method of claim 1, wherein X of the purine derivative of formula (IV) is chloro or benzyloxy group.

5. The method of claim 1, wherein the Mitsunobu reaction is conducted in the presence of triphenylphosphine and di(C$_1$ to C$_6$ alkyl)azodicarboxylate.

6. The method of claim 1, wherein the α-exomethylene derivative of formula (II) is prepared by conducting a Mitsunobu reaction of a β-exomethylene derivative of formula (VII):

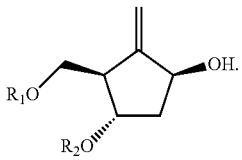

(VII)

7. The method of claim 6, wherein the Mitsunobu reaction is conducted by subjecting the β-exomethylene derivative of formula (VII) to a reaction with triphenyl phosphine and di(C$_1$ to C$_6$ alkyl)azodicarboxylate.

8. The method of claim 6, wherein the β-exomethylene derivative of formula (VII) is prepared by hydrolyzing an epoxide derivative of formula (VIII):

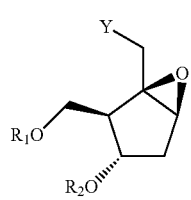

(VIII)

wherein, Y is alkylsilyl or arylsilyl.

9. The method of claim 8, wherein the epoxide derivative of formula (VIII) is prepared by subjecting a compound of formula (IX) to a reaction with peroxide:

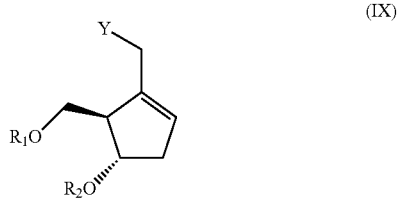

(IX)

10. The method of claim 9, wherein the peroxide is selected from the group consisting of m-chloroperoxybenzoic acid, hydrogen peroxide, t-butyl hydroperoxide, osmium tetroxide, sodium periodate, and a mixture thereof.

11. The method of claim 9, wherein the compound of formula (IX) is a crystalline solid.

12. The method of claim 9, wherein the compound of formula (IX) is prepared by subjecting a triflic enolate derivative of formula (X) to a reaction with alkylsilylmethyl magnesium chloride or arylsilylmethyl magnesium chloride in the presence of a metallic catalyst:

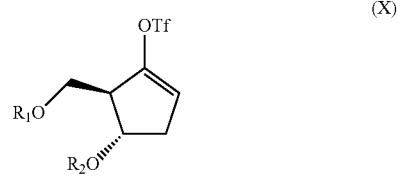

(X)

wherein, Tf is trifluoromethane sulfonyl.

13. The method of claim 12, wherein the metallic catalyst is tetrakis(triphenylphosphine)palladium.

14. The method of claim 12, wherein the triflic enolate derivative of formula (X) is prepared by conducting a reaction of a compound of formula (XI) with a triflating agent in the presence of a base:

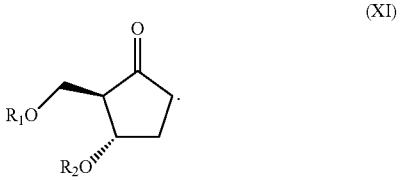

(XI)

15. The method of claim 14, wherein the reaction is conducted at a temperature ranging from 20° C. to −29° C.

16. The method of claim 14, wherein the base is selected from the group consisting of lithium hexamethyldisilazane, potassium hexamethyldisilazane, sodium hexamethyldisilazane, lithium diisopropylamide, n-(C$_1$ to C$_6$ alkyl)lithium, lithium tetramethylpiperidide, potassium butoxide, potassium pentoxide, potassium amylate, and a mixture thereof.

17. The method of claim 14, wherein the triflating agent is selected from the group consisting of trihalomethane sulfonic anhydride; triflimide having a C$_1$ to C$_6$ alkyl or a C$_6$ to C$_{18}$ aryl N-substituent; and a mixture thereof.

18. The method of claim 14, wherein the compound of formula (XI) is prepared by a method comprising the steps of:

preparing a cyclopentanol compound of formula (XIII) as a crystalline solid by treating a cyclopentene derivative of formula (XII) with (+)-diisopinocampheyl borane and H₂O₂, extracting the resulting mixture with a hydrocarbon-based solvent to induce the separation of an organic layer, washing the separated organic layer with a mixture of water and alcohol, and inducing the crystallization of the compound of formula (XIII) by adding a solvent as a crystallization aid; and conducting oxidation of the cyclopentanol compound of formula (XIII) with a mixture of pyridine.SO₃ complex, trialkylamine, and dimethylsulfoxide:

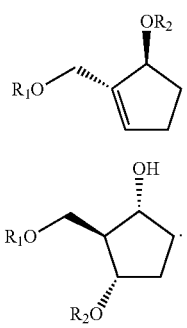

(XII)

(XIII)

19. The method of claim 18, wherein the washing process is conducted three or more times by using a mixture of water and alcohol mixed in a weight ratio ranging from 1:1 to 1:3.

20. The method of claim 18, wherein the washing process is conducted five times by using any of the mixtures of water and alcohol having a mix weight ratio of 1:1, 1:1.5, 1:2, 1:2.5, or 1:3.

21. The method of claim 18, wherein the solvent used as the crystallization aid is selected from the group consisting of hexane, heptane, octane, methanol, ethanol, isopropyl alcohol, water, and a mixture thereof.

22. The method of claim 1, which further comprises the step of:

treating the compound obtained from the hydrolysis of step (d) with dimethylformamide to obtain a crystalline solvate form of entecavir dimethylformamide of formula (XIV); and re-crystallizing the solvate of entecavir dimethylformamide of formula (XIV) from water:

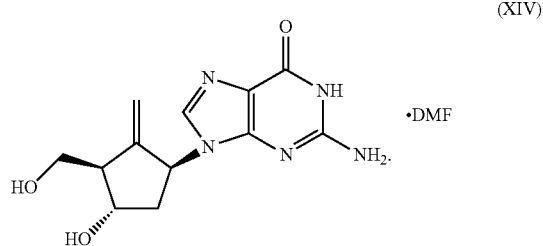

(XIV)

23. A solvate of crystalline entecavir dimethylformamide of formula (XIV) whose X-ray diffraction spectrum obtained using Cu-Kα radiation shows peaks having a peak intensity of 10% or more at diffraction angles (2θ±0.2) of 10.2, 14.4, 14.5, 16.6, 17.9, 18.8, 19.3, 19.8, 21.4, 21.9, 24.5, 25.5, 25.8, 26.7, 29.3, and 30.2:

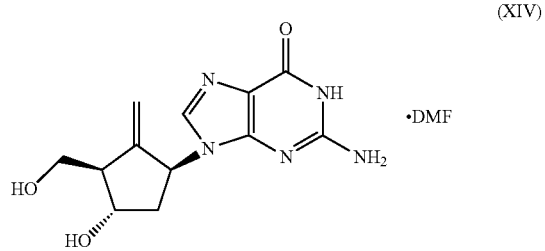

(XIV)

wherein, DMF is dimethylformamide.

24. A method for preparing the solvate of crystalline entecavir dimethylformamide of claim 23, comprising the steps of: dissolving the entecavir compound of formula (I) in a solvent containing dimethyl formamide; and inducing the crystallization of the compound of formula (XIV) therefrom:

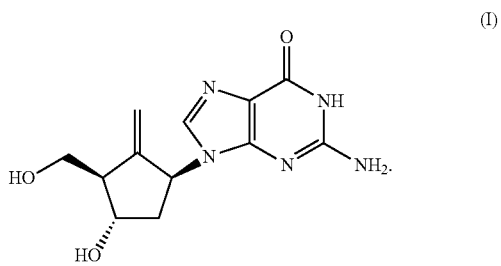 [SMILES: C=C1[C@H](CO)[C@@H](O)C[C@@H]1n1cnc2c(=O)[nH]c(N)nc21]

(I)

* * * * *